United States Patent [19]

Culshaw et al.

[11] Patent Number: 5,296,374
[45] Date of Patent: Mar. 22, 1994

[54] APPARATUS FOR ASSESSING A PARTICULAR PROPERTY IN A MEDIUM

[75] Inventors: Brian Culshaw, Kilmacolm, Scotland; Anthony P. F. Turner, North Crawley, England

[73] Assignee: University of Strathclyde, Glasglow, Scotland

[21] Appl. No.: 847,009

[22] PCT Filed: Oct. 19, 1990

[86] PCT No.: PCT/GB90/01615

§ 371 Date: Apr. 22, 1992

§ 102(e) Date: Apr. 22, 1992

[87] PCT Pub. No.: WO91/05999

PCT Pub. Date: May 2, 1991

[30] Foreign Application Priority Data

Oct. 20, 1989 [GB] United Kingdom ............... 8923699

[51] Int. Cl.⁵ .................. C12M 1/40; C12M 1/34
[52] U.S. Cl. .......................... 435/288; 435/291; 422/82.05; 422/82.12; 374/31; 374/117
[58] Field of Search .............. 435/287, 288, 291, 807, 435/808, 817; 422/68.1, 82.01, 82.05, 82.11, 82.12, 51; 374/31, 117, 118, 32

[56] References Cited

U.S. PATENT DOCUMENTS

| | | | |
|---|---|---|---|
| 4,354,482 | 8/1982 | Adolfsson et al. | 374/117 |
| 4,541,731 | 9/1985 | Bell et al. | 374/117 |
| 4,650,346 | 3/1987 | Tehon | 374/117 |
| 4,874,252 | 10/1989 | Ziegler et al. | 374/117 |
| 4,935,345 | 6/1990 | Guilbeau et al. | 435/788 |
| 5,017,494 | 5/1991 | Karube et al. | 435/288 |

FOREIGN PATENT DOCUMENTS

| | | | |
|---|---|---|---|
| 0352676 | 1/1990 | European Pat. Off. | 374/117 |
| 2415997 | 10/1974 | Fed. Rep. of Germany . | |
| 3744239 | 6/1989 | Fed. Rep. of Germany | 374/117 |
| 2359419 | 2/1978 | France . | |
| 0057926 | 5/1981 | Japan | 374/117 |
| 0052535 | 3/1983 | Japan | 374/117 |
| 0148335 | 7/1986 | Japan | 374/117 |
| 0145539 | 6/1989 | Japan | 374/117 |
| 0221628 | 9/1989 | Japan | 374/117 |
| 0250027 | 10/1989 | Japan | 374/117 |
| 8907753 | 8/1989 | PCT Int'l Appl. . | |
| 9000203 | 1/1990 | PCT Int'l Appl. | 435/288 |
| 0540157 | 12/1976 | U.S.S.R. | 374/117 |
| 0620836 | 7/1978 | U.S.S.R. | 374/117 |
| 0649966 | 5/1979 | U.S.S.R. | 374/117 |
| 1151836 | 4/1985 | U.S.S.R. | 374/117 |

OTHER PUBLICATIONS

Mosbach et al. "Thermal bioanalyzers in flow streams enzyme thermistor devices" Analytical Chem., vol. 53, No. 1 (Jan. 1981) pp. 83;84;86;89–91, 94.

Xie et al. "A versatile thermal biosensor" Sensors and Actuators, vol. 19, No. 1 (Aug. 1989) pp. 53–59.

Primary Examiner—Michael G. Wityshyn
Assistant Examiner—William H. Beisner

[57] ABSTRACT

A sensor is provided which is sensitive to a particular property of a medium and which is thermally activated when in contact with the property containing medium. The sensor is externally mounted on the undersurface of a silicon wafer, the upper surface of which contains a well in which a vibratile bridge element is located. The top of the well is closed off so that the vibratile bridge element is within a chamber. Excitation energy from a source is delivered to the vibratile bridge element to establish vibratory motion which is monitored and detected by a circuit. Presence of the particular property in the medium causes a thermal change in the wafer resulting in a change in the resonance frequency of the vibratory motion of the vibratile bridge element. The frequency shift is a measure of the particular property.

6 Claims, 3 Drawing Sheets

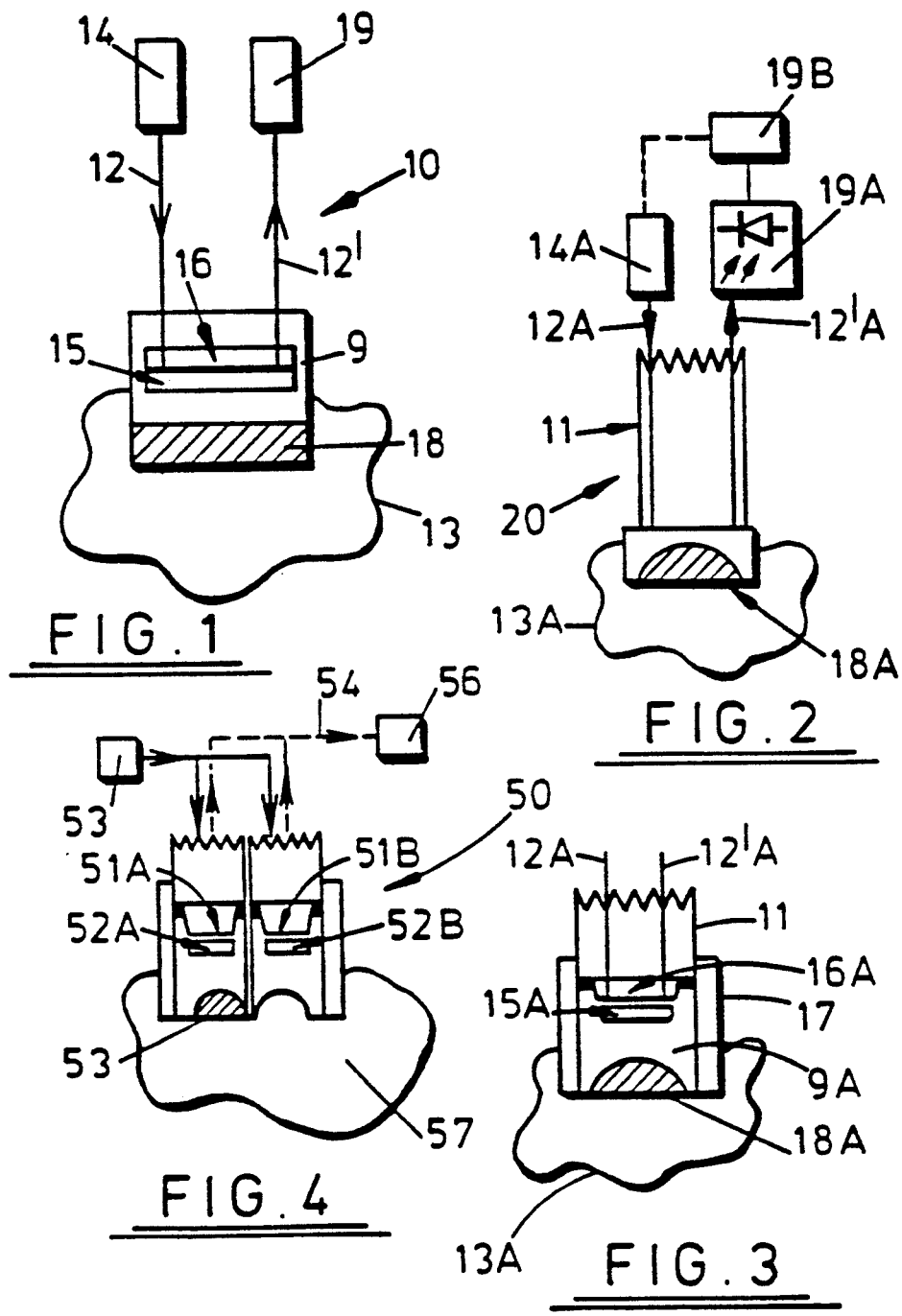

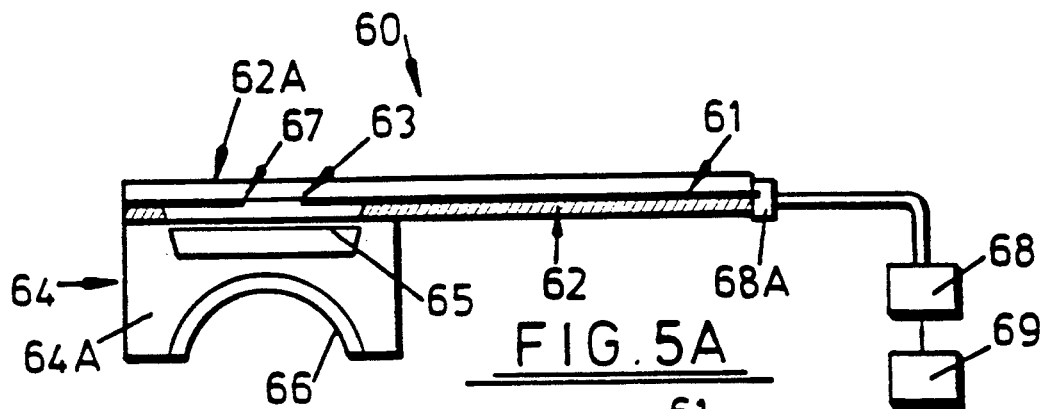
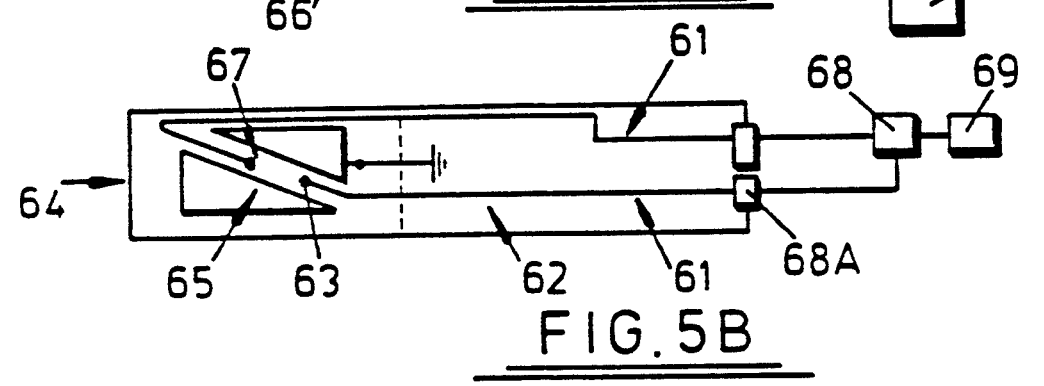
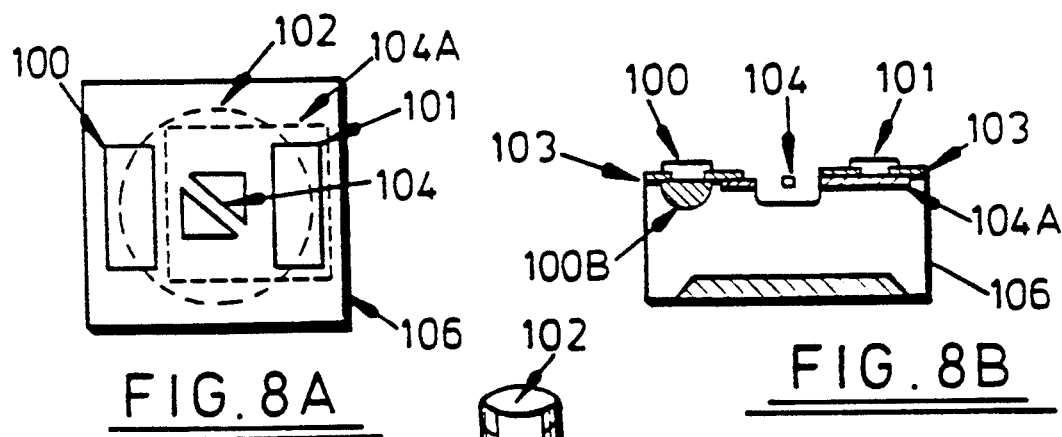
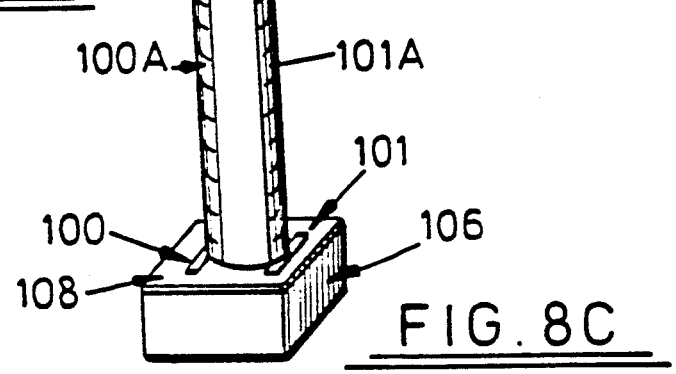

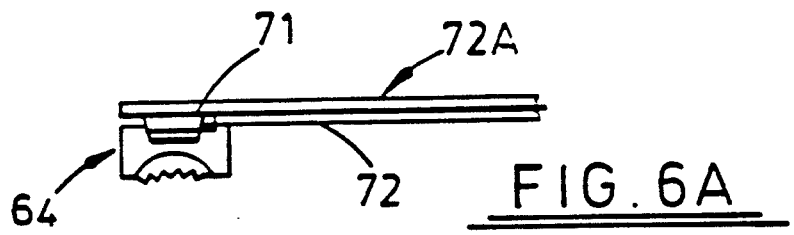
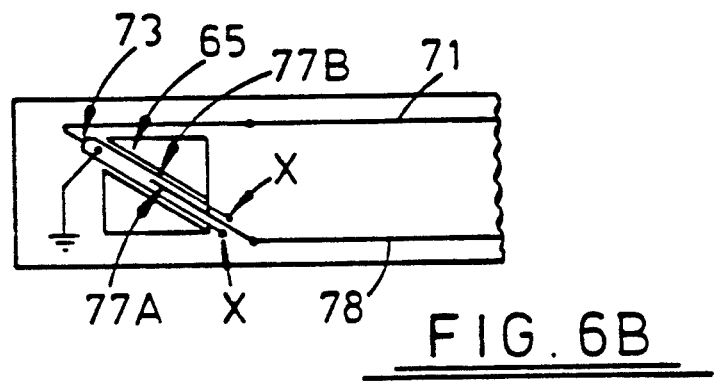
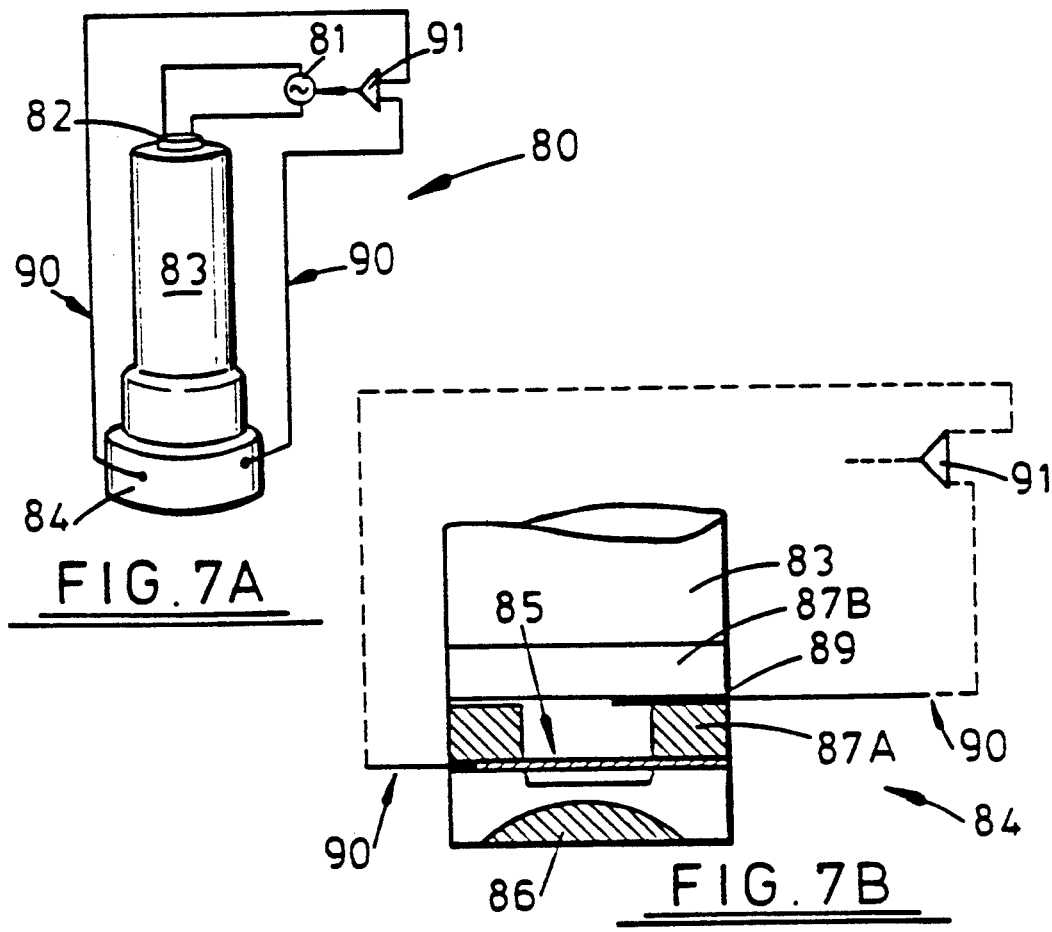

APPARATUS FOR ASSESSING A PARTICULAR PROPERTY IN A MEDIUM

FIELD OF THE INVENTION

This invention relates to an apparatus for assessing a property of a medium, particularly but not exclusively a fluid medium.

BACKGROUND OF THE INVENTION

A known form of apparatus for assessing a property of a fluid comprises an optical fiber coated near its tip with an enzyme or antibody. When the coated tip is contacted with the fluid, enzyme-catalyzed reactions create localized heating and expansion of the fiber and the rate of expansion, ana hence the rate of reaction, is measured by comparing the fiber length with that of an adjacent reference fiber using interferometry. The known apparatus is not temperature stable and operation depends on the expansion of an optical fiber which is a disadvantage where space is limited.

SUMMARY OF THE INVENTION

It is an object of the present invention to provide a new and improved form of apparatus for assessing a property of a medium in which the aforementioned disadvantages are obviated or substantially mitigated. This is achieved by using an apparatus wherein localized heating, created for example by a chemical reaction, causes the resonant frequency of a vibrating member to change, the change in frequency being an assessment or measure of the property.

According to the present invention there is an apparatus for assessing a particular property of a medium, comprising at least one vibratile element located within a closed chamber and mounted on a structure part of which structure forms said chamber, means for delivering excitation energy to said vibratile element to cause the element to vibrate at its resonant frequency, means for monitoring and detecting the vibration frequency of the vibratile element, and sensor means mounted on an exterior surface of the chamber structure to enable contact with the medium, the sensor means being thermally activated when contacted with a medium having the particular property whereby to change the temperature of the chamber and hence the resonant frequency of the vibratile element, which change as monitored and detected by the monitoring and detecting means provides an assessment o the presence of the particular property of the medium.

The property of the medium may be temperature, biomass, pH or dissolved gas content. Alternatively the property may be the presence in the medium of a natural or synthesized chemical or biological species e.g. an antibody, an antigen, or a barbiturate capable of being conjugated with a sensor means which includes an enzyme.

The energy is preferably light but may alternatively be electrical or ultrasound.

The vibratile element may be fabricated from a semiconductor wafer and when optical excitation is used may be disposed relative to an optical fiber delivery means to form a Fabry-Perot cavity so that the element is self-oscillating when the energy is continuous or the element may be maintained in resonant oscillation, (without forming a cavity with the delivery means by a feedback drive system applied to the delivery means.

Furthermore, when the delivery means delivers electrical energy a pattern of conductive electrodes having tracks linking the delivery means and collecting means may overlie the vibratile element and be so arranged as to stimulate the vibratile element into resonant oscillation and detect the oscillations using electrostatic and/or electromagnetic forces. Where this arrangement is used the vibratile element is made of conductive material and may or may not be current carrying.

The substrate of the structure may be N type locally N+ doped and contact may be made by virtue of a metallization applied to the N+ contact diffusion which in turn may be positively charged. A further metallization which is negatively charged may be in contact with a P+ doped layer of which the vibratile element forms part. The metallization may be connected to a voltage source through a silica post having disposed on its surface metal tracks which at the supply end are in contact with the voltage source and at the other end are connected to said N+ and P+ layers.

The delivery means and the collecting means may include fiber light guide means or an acoustic guiding medium. The, or each fiber light guide means may comprise a single optical fiber fused or otherwise bonded to the chamber structure. Alternatively the delivery means and collecting means may include a combination of the acoustic guide and conductive tracks providing a feedback drive system. The feedback drive system may also include a high gain amplifier and a counter.

The sensor means may be chemically reactive with the medium an exothermic or an endothermic manner and may comprise an enzyme selected so that the particular property to be assessed is the substrate of the enzyme. The sensor means may include a diffusion barrier. The sensor means may be in the form of a coating on the exterior of the chamber structure. The coating may be replaceable.

High concentrations of a property in a chemical are difficult to measure with enzymic reactions since there is non-linearity between the rate of exothermic reaction and substrate concentration. Such substrates can be measured by including a diffusion barrier in the sensor means between the catalyst and the medium to be assessed thus reducing 'apparent' concentrations as viewed by the catalyst. A typical diffusion barrier is a chemically inert plastic membrane.

It will be appreciated that a sensor means which will cause local changes in temperature during a chemical reaction can be found for most naturally occurring and some synthetic chemicals and biological species and a number of different properties can therefore be assessed.

By virtue of being closed the chamber is impenetrable to moisture. The chamber may also be evacuated. The apparatus, particularly the closed chamber structure, may be thermally insulated other than at the location of the sensor means.

Embodiments of the invention can be used in a broad range of applications from continuous monitoring of process control in the food and fermentation industries measuring, for example, temperature and pH, to discrete sample analysis in human diagnostics where there is a need for rapid results to complement the clinical history and examination of patients in hospitals.

Embodiments of microminiature construction are very portable and this can be important, for example, for use by mobile medical teams. Microminiature size also permits use on internal parts of the body where access is difficult and as in microsurgery. The sensor structures can be batch fabricated to reduce the overall cost of the device.

BRIEF DESCRIPTION OF THE DRAWINGS

Embodiments of the present invention will now be described by way of example with reference to the accompanying schematic drawings, in which:

FIG. 1 illustrates an apparatus according to the present invention in diagrammatic form;

FIG. 2 illustrates a preferred embodiment of the present invention;

FIG. 3 shows a part of the FIG. 2 embodiment in more detail;

FIG. 4 illustrates a further embodiment of the present invention.

FIGS. 5A and 5B show side and plan views of a further embodiment of the present invention using an electrostatic drive;

FIGS. 6A and 6B show a further embodiment of the present invention using an electromagnetic drive;

FIGS. 7A and 7B show yet a further embodiment of the present invention using an ultrasonic drive; and FIGS. 8A, 8B and 8C show a modified version of the embodiment described in FIGS. 5A and 5B.

DESCRIPTION OF THE PREFERRED EMBODIMENT

With reference to FIG. 1 an apparatus 10 for assessing a particular property of a medium 13 utilized energy 12 originating from a delivery means 14 and incident the vibratile element 16 located within a closed chamber 15. Element 16 is mounted a structure 9 forming the chamber 15 and is caused to vibrate at its resonant frequency by the energy 12. Sensor means 18 mounted on an exterior surface of the structure 9 is capable of being thermally activated and causes changes in temperature of the structure 9 when contacted with the particular property of the medium 13 to which the sensor means is sensitive. The changes in temperature of the structure 9 cause the resonant frequency of the vibratile element 16 to change so that vibration sensing energy 121 (which may be the reflected excitation energy 12 or energy from a separate source) is modulated at the new resonant frequency of the element 16 which is detected by collecting means 19. The resonant frequencies of the vibratile element 16 prior to and after the temperature change caused by the sensor means 18 contacting the medium 13 are compared and the change is an assessment of the presence of the particular property of the medium 13.

FIG. 2 and FIG. 3 show a preferred embodiment 20 of the present invention for assessing the concentration of hydrogen peroxide in a fluid medium 13A. Energy, conveniently being light 12A originating from a laser light source 14A, is directed through an optical fiber waveguide 11 and onto vibratile element 16A fabricated from a semiconductor wafer 9A. The light 12A is synchronized, for example by being pulsed at a repetition rate controlled using the modulation of reflected light 12'A to operate a feedback loop, to cause the element 16A to vibrate continuously at its resonant frequency.

Element 16A is a bridge formed by undercutting (or tunnelling) beneath the floor of a depression or well formed in the silicon wafer and the chamber 15A containing element 16A is closed by the upper surface of the wafer 9A being adherent to the waveguide 11. Element 16A is physically isolated from the medium 13A by the remaining thickness of wafer 9A so that the physical characteristics (e.g. viscosity) of the medium 13A do not directly influence the motion of the element 16A. The wafer 9A is generally enclosed and thermally isolated by a laterally-extending barrier 17 which may be formed of one or more oxides of silicon. Sensor means 18A, in the form of a polymerized gel containing a chemical catalyst such as catalase, is disposed on the non-thermally enclosed exterior surface of the wafer 9A and reacts in an exothermic manner on contact with hydrogen peroxide in the medium 13A causing a change in temperature in the chamber structure.

The structure shown in FIG. 3 is preferably fabricated from a silicon wafer 750 microns thick with a 500 micron diameter hemispherical cavity formed (by etching) in its under surface to receive the sensor means 18A and the vibratile element 16A is a beam etched at a distance below the top surface of the wafer. Typically this provides a chip 750×750 microns in area. The lateral external surfaces of the chip are thermally insulated with a layer 17 of silicon oxide resulting in minimal surface area of the chip in contact with the medium 13A but maximum contact with the gel containing the catalase. Accordingly, heat generated by the catalase in reacting with its hydrogen peroxide substrate is preferentially directed into the silicon wafer 9A, the thermal conductivity of which is relatively high, so that a measurable temperature change in the chip results. For example, with a silicon oxide coating 100 microns in thickness temperature changes of the order of 1° K. are readily obtained. Substantially higher temperature changes arise when polystyrene is substituted for the silicon oxide. A preferred form of the FIG. 3 structure fabricated from a silicon wafer has its undersurface cavity of truncated pyramidal form (since this is easier to etch than hemispherical) and the well formed beneath the vibratile element is also of truncated pyramidal form. The vibratile element may be a beam with a single span or a beam with a double span (thereby forming a type of double tuning fork resonant structure).

Waveguide 11 is a single optical fiber fused via a suitable bonding material to the silicon wafer 9A. Light 12$A reflected from the element 16A is collected by the waveguide 11 and detected by a photodiode 19A. Using known electronic equipment 19B connected to the photodiode 19A the initial resonant frequency of the vibratile element 16A and the changed resonant frequency are compared. From this comparison the rate of chemical action between the catalase 18A and the hydrogen peroxide is determined and for a known concentration of catalase the concentration of hydrogen peroxide in the medium 13A can be found.

The apparatus which has been described with reference to FIG. 3 is microminiature in size and is low in thermal mass so that it responds rapidly e.g., in about 100 micro-seconds to temperature changes as low as or lower than $1 \times 10^{-3}$ Kelvin degrees.

FIG. 4 shows a further embodiment 50 of the present invention for providing a method of assessing a particular property of a medium 57 when variations in the ambient temperature of the medium 57 are expected. The embodiment 50 has two adjacent vibrating elements 51A, 51B respectively located within separate closed chambers 52A, 52B formed by individual silicon wafers and bonded optical fibers. A single thermal barrier surrounds and unifies the two structures. Light originating from light delivery means 53, conveniently a laser, is delivered to both chambers to excite both elements 51A, 51B into resonance and is reflected (54) from the vibrating elements 51A, 51B, to be detected by light collecting means 56. Sensor means 55 are disposed on an exterior surface of the structure forming chamber 52A and affect the vibratile element 51A in a fashion similar to that of the embodiment shown in FIG. 2 and FIG. 3 (i.e. being affected by both the temperature of the medium 57 and by the particular property of the medium to which the sensor means 55 are sensitive) but sensor means are absent from the exterior surface of the structure forming chamber 52B so that the vibratile element 51B will be affected only by the ambient temperature of the medium 57. Any changes in the ambient temperature of the medium 57 can therefore be separately detected and subtracted to give a temperature-independent assessment of the property of the medium.

FIGS. 5A and 5B show in side and plan views an electrostatically driven resonant biosensor 60. Biosensor 60 comprises a silicon wafer 64A carrying sensor means 66 and vibratile element 65 the top surface of which is contiguous with the top surface of the wafer 64A. Secured to the top surface of the wafer 64A (but not to the element 65) is a structure which incorporates an interrupted conductive electrode 61 which is arranged, at least in part, to overlie the element 65. Electrode 61 is evaporated onto an oxidized silicon carrier 62A and is covered by a layer 62 of oxidized silicon which has a window in registry with the well in wafer 64A containing the element 65. Secural of the conductor support to the wafer is preferably by bonding. Conveniently the conductor support is of smaller bulk than the structure which incorporates the vibratile element and the layer 62 is thermally insulating material which acts so as to minimize heat loss by conduction. Additionally, conductive electrode 61 is of minimal cross section. The electrode 61 extends along support 62A from a terminal 68A and terminates at a point 63 which overlies the vibratile element 65. The electrode 61 continues from a point 67 spaced from point 63 and connects to a high gain amplifier 68 and counter 69. The wafer 64A is N+ and the vibratile element 65 is doped with boron so as to be P+ and is earthed. Application of a voltage V (which initially may be a noise voltage) to the drive part of the electrode 61 electrostatically deflects the P+ doped element 65 due to the capacitance between the conductor part containing point 63 and the element 65. This deflection is monitored using the changing capacitance that is consequently established between the conductor part containing point 67 and the conductive element 65. The change in charge in the sensing part of the electrode 61 due to the varying capacitance is amplified by amplifier 68 and feedback to the terminal 68A and the circuit effectively becomes an oscillator. The oscillating circuit is connected to a counter 69 which counts the number of deflections of the vibratile element 65 per unit time.

As discussed in earlier embodiments when in contact with an appropriate medium sensor 66 which is coated on to substrate 64A, causes localized heating in the structure 64 so that the vibrational frequency of the element 65 changes which is monitored by the capacitance between 67 and 65. The change in oscillation frequency of the oscillator is counted on the counter 69 and compared with earlier values to give an assessment of the property in the medium.

FIGS. 6A and 6B show yet a further embodiment of the present invention wherein the excitation energy is still electrical as in FIGS. 5A and 5B but the forces causing deflection of the vibratile element are electromagnetic rather than electrostatic. The structure 64 is similar to that of FIGS. 5A and 5B but the conductor which overlies the structure 64 has a different layout and is electrically connected to the vibratile element 65 so that electrical current flows through element 65. The conductive electrode 71 is evaporated onto an oxidized silicon carrier 72A and has a covering 72 of silicon oxide over most of its extent but in the region of the vibratile element 65 the covering 72 is absent. Conductor 71 has a current drive end 73 which is bifurcated into parallel conductor parts 77A, 77B which overlie and extend along the length of the vibratile element 65 being spaced therefrom by the thickness of the covering 72. However, at their ends remote from point 73 parts 77A, 77B extend across the thickness of covering 72 and into electrical contact at points X with the P+ region of the structure 64 adjacent one end of the element 65. The other end of element 65 is connected to earth. Thus, drive end 73 carries two parallel flows of current in one direction while element 65 carries the total current flow in the opposite direction and accordingly the element 65 is stimulated electromagnetically into resonance with suitable pulsing of the current flow. It will be appreciated that although it would be possible to use a single lead in the drive end 73, the alignment of the lead would cause the vibratile element to move in a "skew" fashion and this is undesirable. A second conductive electrode 78 evaporated onto the carrier 72A functions as an electrostatic movement detector in a manner similar to that explained with reference to FIGS. 5A, 5B for conductor portion containing point 67.

FIGS. 7A and 7B show an ultrasonic biosensor 80 which has an oscillator 81 connected to an ultrasonic transducer 82 located at the top of a waveguide 83 which at its lower end has a head 84 shown in detail in FIG. 7B. The head 84 comprises a wafer having a vibratile element 85 which is doped with boron so as to be P+ as in the aforementioned embodiments. A sensor 86 has its outer surface in contact with a medium to be assessed. A first layer of oxidized silicon 87A is disposed on the top surface of the wafer except for the area above the element 85. A single conductive metallic strip 89 is evaporated onto the underside of a second silicon oxide layer 87B which overlies the first layer 87A and the upper surface of the second silicon layer 87B is interfaced with the waveguide 83. Ultrasonic waves generated by the transducer 82 at a frequency determined by the oscillator 81 pass down the waveguide 83 and excite the vibratile element 85 into resonant oscillation. The change in capacitance between the vibratile element 85 (which has vertical movement), and the metallic strip 89 due to the element's vibration will be detected since both the vibratile element 85 and strip 89 are connected to a detection system via wires 90.

To maintain oscillation of the element 85 the detection system is connected to a feedback drive system having an amplifier 91 which provides a control signal to the oscillator 81 if the frequency of the ultrasonic waves requires to be altered. It will be appreciated that, although not shown, a counter can be connected in parallel with the amplifier and oscillator to give a reading of the frequency of oscillation of the element. Silica is capable of conducting light and ultrasound equally efficiently, and if, for example, waveguide 83 is an optical fiber made of silica then optical detection of the vibration could be incorporated with the ultrasonic excitation.

A modified version of the embodiment of the invention described in FIGS. 5A, 5B is shown in FIGS. 8A, 8B, 8C wherein the excitation is electrical. In FIG. 8B an N type substrate 106 has an under surface cavity for carrying the property-sensing means and an under surface well incorporating the resonant element in the form of a bridge 104. The bridge 104 forms part of a P+ doped region 104A diffused into part of the substrate 106. Also diffused into substrate 106 is an N+ contact diffusion layer 100B but which is spaced from P+ region 104A so that a P-N junction is formed. A conductive metal pad 100 is deposited onto layer 100B and a conductive metal pad 101 is deposited onto region 104A and a D.C. bias voltage is applied to these pads 100, 101 in order to excite the vibratile element 104 into vibration. The bias voltage is delivered to the pads 100, 101 via metal tracks 100A, 101A formed on the surface of a silica post 102 the lowermost end of which forms a cover for the well containing the bridge 104 and which is spaced above the bridge 104 by an intervening layer of silicon 103. The exterior surfaces of the assembly are covered with a thermal insulation layer 108 which may be made of polystyrene.

It will be appreciated that capacitance occurs at the junction between the substrate 106 and the region 104A so that changes in capacitance caused by vibration of the bridge 104 are detectable in a manner similar to that of FIG. 5.

It will be appreciated that the material-property-sensing structure is common to all embodiments of the present invention; the excitation delivery and vibration-signal collecting means can be varied. Optical, electrostatic, electromagnetic and ultrasonic systems have been disclosed.

The area of the sensing head is microminiature and effectively measures a single point in the medium. When the medium has a larger volume than a single point measurement may be unrepresentative of the bulk. By multiplexing a number of sensors located throughout the medium or by increasing the effective area of the sensing head a more accurate assessment of a property of the medium can be made.

To further improve the accuracy of readings a thermally insulating sleeve could be disposed over the entire apparatus minimizing any heat loss to ambient. Sensitivity could be varied by changing the material and coefficient of thermal expansion of the vibratile element.

It will be appreciated that in the foregoing embodiments utilizing optical excitation the reflected light which is collected by the collecting means emanates originally from the delivery means the principal purpose of which is to excite the element into oscillation. However, whether using optical, acoustic or electrical excitation the collecting means may collect reflected light emanating from a separate light source provided specifically for the collecting and measuring system in the manner described in International Patent Specification No. Wo 86/05271.

What is claimed is:

1. An apparatus for assessing a particular property of a medium comprising:
    a chamber having a thermally conductive portion;
    a vibratile element thermally coupled within said chamber to said thermally conductive portion;
    optical excitation means for delivering optical excitation energy incident to said vibratile element so as to cause the vibratile element to vibrate at its resonant frequency without inducing thermal changes in the chamber;
    optical means for monitoring and detecting the vibration frequency of the vibratile element; and
    thermally activated sensor means, thermally coupled to an exterior surface of said thermally conductive portion thereby being exposed to enable contact between said thermally activated sensor means and the medium, said thermally activated sensor means being a material which is thermally activated when contacted with said medium having said particular property for changing the temperature of the chamber and hence the resonant frequency of the vibratile element by heat transfer through the thermally conductive portion between the thermally activated sensor means and the chamber, said changes in said resonant frequency being monitored and detected by the optical means which provides an assessment of the presence of said particular property of said medium.

2. An apparatus according to claim 1, wherein the thermally activated sensor means is chemically reactive with the medium in an exothermic or an endothermic manner.

3. An apparatus according to claim 1, wherein the thermally activated sensor means comprises an enzyme selected so that the particular property to be detected is the substrate of the enzyme.

4. An apparatus according to claim 3, wherein the thermally activated sensor means comprises a diffusion barrier.

5. An apparatus according to claim 1,
    wherein the thermally conductive portion is a semiconductor wafer segment having two wells therein, said vibratile element being formed within a first well in the upper surface of the wafer segment and said thermally activated sensor means being located in a second well in the lower surface of the wafer segment.

6. An apparatus according to claim 5, further comprising an optical fiber, coupled to the upper surface of the wafer segment and overlying said first well therein, said optical fiber being provided for the delivery of the optical excitation energy and for the monitoring and detecting of the vibration frequency of the vibratile element.

* * * * *

UNITED STATES PATENT AND TRADEMARK OFFICE
CERTIFICATE OF CORRECTION

PATENT NO. : 5,296,374
DATED : March 22, 1994
INVENTOR(S) : Brian Culshaw and Anthony P.F. Turner It is certified that error appears in the above-identified patent and that said Letters Patent is hereby corrected as shown below:

On the title page, in items [75] and [56]:

Assignee: "Glasglow" should be -- Glasgow --.

References, "4,354,482" should be -- 4,345,482 --.

References, first publication, the semicolons ";" should be commas -- , --.

Column 1, line 50, "o" should be -- of --.

Column 1, line 67, after "means" insert a parenthesis -- ) --.

Column 2, line 23, after "each" insert a comma -- , --.

Column 2, line 31, after "medium" insert -- in --.

Column 3, line 30, "utilized" should be -- utilizes --.

Column 3, line 32, "the" should be -- to a --.

Column 3, line 33, after "mounted" insert -- on --.

Column 3, line 43, "121" should be -- 12' --.

Column 4, line 43, "12$A" should be -- 12'A --.

UNITED STATES PATENT AND TRADEMARK OFFICE
CERTIFICATE OF CORRECTION

PATENT NO. : 5,296,374
DATED : March 22, 1994
INVENTOR(S) : Brian Clushaw and Anthony P.F. Turner It is certified that error appears in the above-indentified patent and that said Letters Patent is hereby corrected as shown below:

Column 7, line 5, "under" should be --upper--.

Signed and Sealed this

Nineteenth Day of July, 1994

Attest:

BRUCE LEHMAN

*Attesting Officer*   *Commissioner of Patents and Trademarks*